(12) United States Patent
Itai et al.

(10) Patent No.: US 7,286,940 B2
(45) Date of Patent: Oct. 23, 2007

(54) METHOD OF PREDICTING FUNCTIONS OF PROTEINS USING LIGAND DATABASE

(75) Inventors: Akiko Itai, 5-16-6, Hongo, Bunkyo-ku, Tokyo (JP) 113-0033; Masazumi Imamura, Chiba (JP)

(73) Assignee: Akiko Itai, Tokyo (JP)

( * ) Notice: Subject to any disclaimer, the term of this patent is extended or adjusted under 35 U.S.C. 154(b) by 0 days.

(21) Appl. No.: 09/985,652

(22) Filed: Nov. 5, 2001

(65) Prior Publication Data

US 2002/0155501 A1 Oct. 24, 2002

Related U.S. Application Data

(63) Continuation of application No. 09/446,897, filed as application No. PCT/JP98/02986 on Jul. 2, 1998, now abandoned.

(30) Foreign Application Priority Data

Jul. 3, 1997 (JP) ................................. 9-177933

(51) Int. Cl.
*G01N 33/48* (2006.01)
(52) U.S. Cl. ..................................... 702/19
(58) Field of Classification Search .................. 435/6; 530/350, 300; 702/19, 27; 706/45
See application file for complete search history.

(56) References Cited

U.S. PATENT DOCUMENTS

| 5,642,292 | A | 6/1997 | Itai et al. |
| 6,308,145 | B1 | 10/2001 | Itai et al. |
| 6,389,378 | B2 | 5/2002 | Itai et al. |
| 6,490,588 | B2 | 12/2002 | Itai et al. |
| 2003/0061198 | A1 | 3/2003 | Itai et al. |
| 2004/0137432 | A1 | 7/2004 | Itai et al. |

FOREIGN PATENT DOCUMENTS

| EP | 0790567 | 8/1997 |
| JP | 2-200641 | 8/1990 |
| WO | 93/20525 | 10/1993 |
| WO | 96/13785 | 5/1996 |
| WO | 97/18180 | 5/1997 |
| WO | 9724301 | 10/1997 |

OTHER PUBLICATIONS

Rahaman et al., "IL-13Ralpha2, a Decoy Receptor for IL-13 Acts as an Inhibitor of IL-4-dependent Signal Transduction in Glioblastoma Cells," Cancer Research, Feb. 2002, vol. 62, pp. 1103-1109.*
Tomioka, N. and Itai, A.,J. Computer-Aided Mol. Design, vol. 8, 347-366 (1994).
Mizutani, M. et al., J. Mol. Biol., vol. 243, 310-326 (1994).
English Abstract for Appl. WO97/24301, listed in International Search Report.
Martin, Yvonne C., Database accension No.: 114:80616 CA XP002196005.
Moon, J., and Howe, W., Proteins:, Structure., Funct., Genet. 11(4), pp. 314-328 (1991).
Boehm, Hans J., Database accenssion No.: 119:66291 CA XP002196006.
Boehm, Hans J., J. Computer-Aided Mol. Des. 6, pp. 61-78 (1992).
Kagaku Zohan 113, "Protein engineering - Design and synthesis of new proteins", edited by Funio Sakiyama and Ken'ichi Matsubara, KK Kagaku Doin, Mar. 25, 1988, pp. 125-135.
English Language Abstract of JP 2-200641.
Yamada, M. et al. "Development of an efficient automated docketing method," Chem. Pharm. Bull., (1993) 41(6) pp. 1200-1202.
Yamada, M. et al. "Application and evaluation of the Automated docketing method" Chem. Pharm. Bull. (1993) 41(6) pp. 1203-1205.
Katchalski-Katzir, E., et al. "Molecular surface recognition determination of geometric fit between proteins and their ligands by correlation techniques," Proc. Natl. Acad. Sci. USA (1992) 89(6) pp. 2195-2199.
Scherz, M.W. "Synthesis and structure-activity relationships of $N_1N^1$-di-o-tolyguanidine analogues high-affinity ligands for the haloperidol-sensitive sigma receptor," J. Med. Chem. (1990) 33(9) pp. 2421-2429.
Nishibata, Y. "Automation creation of drug candidate structures based on receptor structure. Starting point for artificial lead generation," Tetrahedron, (1991) 47(43) pp. 8985-8990.
Gallop, M.A. et al. "Applications of combinatorial technologies to drug discovery. 1. Background and Peptide Combinatorial Libraries," J. Med. Chem. (1994) 37(9) pp. 1233-1251.
Scott, D. A. et al. "The Penxred syndrome gene encodes a chloride-iodide transport protein", Nature Genetics, (1999), 21 (4), pp. 440-443.
English translation of Kagaku Zohan 113, "Protein engineering - Design and synthesis of new proteins", edited by Funio Sakiyama and Ken'ichi Matsubara, KK Kagaku Doin, Mar. 25, 1988, pp. 125-135.

* cited by examiner

Primary Examiner—Young J. Kim
(74) Attorney, Agent, or Firm—Greenblum & Bernstein, P.L.C.

(57) ABSTRACT

A method of predicting a biological function of one or more query proteins having predetermined or predictable steric structures using a three-dimensional structure database comprising:
  (a) selecting at least one bio-active compound capable of binding to the query protein as ligand candidates from the database based on the capability of complex formation between the query protein and bio-active compound; and
  (b) predicting that a biological function of the query protein are identical or similar to the biological functions of proteins with predetermined biological functions to which the ligand candidates bind,
wherein the database comprises the structure of at least one bio-active compound which binds to proteins with predetermined biological functions.

4 Claims, 2 Drawing Sheets

METHOD OF PREDICTING FUNCTIONS OF PROTEINS USING LIGAND DATABASE

This is a continuation of U.S. application Ser. No. 09/446,897 filed Jul. 2, 1998 which is a National Stage of International Application No. PCT/JP98/02986, filed Jul. 2, 1998, the contents of which are expressly incorporated by reference herein in their entireties. The International Application was not published under PCT Article 21(2) in English.

TECHNICAL FIELD

The present invention relates to prediction methods of the protein functions and databases used for said methods.

BACKGROUND ART

Proteins are biopolymers comprising 20 kinds of amino acids as building blocks and have structures in which about 50 to 1,000 amino acids are connected in a chain by peptide bonds (—CONH—). The existence of various kinds of proteins has been revealed such as enzymes which catalyze substance conversion in organism, receptors related to their inter- or intracellular signal transduction, receptors related to the control of gene expression, cytokines which are secreted at the time of inflammation, proteins related to the transport of substances and others. In the organisms of higher animals such as human, there are 50 to 100 thousands of kinds of proteins, and each plays specific functions and roles.

Enzymes provide fields for chemical reactions in which specific products are obtained by the actions on specific substrates, and proceed stereospecific or regiospecific reactions with moderate conditions. Receptors transduce signals through the structural change upon the binding of hormones and signal transmitters. The features common to these enzymes and receptors are the appearance of their biological functions by forming stable complexes with specific molecules (ligands). Protein molecules, which are long like strings, are folded to take certain steric structures and form structural sites (ligand binding sites) which bind specifically with artificial molecules such as drugs and specific biomolecules. This ligand binding site is essential for the appearances of the functions of enzymes and receptors.

The steric structures of proteins can be determined by X-ray crystallographic analysis and NMR analysis. Due to the remarkable progress and spread of these analytical techniques, determination of steric structures of proteins has become easy, and the number of proteins analyzed is increasing acceleratingly. Protein Data Bank, which is a database of protein structures, stores three-dimensional coordinates of more than 7,000 proteins at present, and the data are available throughout the world. Accordingly, once functions of a protein are known, it has become possible to understand the relations between the structure and the function of the protein on atomic levels by analyzing the crystal structure of the complexes with appropriate ligands. Moreover, by using the steric structures of proteins which have been analyzed crystallographically as templates, and by substituting the side chains of amino acids, it has become possible to predict the steric structure of a protein having highly homologous amino acid sequences (homology modeling).

Protein studies have so far been conducted by the means in which after the separation and purification of proteins employing its biological function as a guide, its amino acid sequence is determined to analyze the structure and function. However, recently, as analyses of genes have become easy, there are cases in which the existence of a protein is suggested from genetic information. For example, the existence of considerable number of proteins has been revealed by a large-scale project aiming at the human genome analysis, and these results are expected to be utilized for the elucidation of the cause of diseases and drug design.

However, for those proteins successively found from genome analysis studies, their amino acid sequences are merely elucidated, while in most cases their biological functions cannot be predicted at all. For this reason, an enormous amount of study is necessary to predict or confirm functions for each protein, which becomes an obstacle for the effective use of genome information. Moreover, although the steric structure of proteins whose amino acid sequences have been elucidated can be determined more easily than before due to the progress of crystallographic analysis and NMR analysis, there are many cases in which the functions are hardly known even though the steric structures of proteins have been elucidated.

At present, methods of predicting the functions of novel proteins easily have not been established. For example, a prediction method is adopted in which a novel protein is predicted to have functions similar to a known protein, if a protein with high homology is found by comparing the amino acid sequence of the novel protein with groups of amino acid sequences of proteins with known functions. Furthermore, for the multiple proteins with the same functions, information concerning the correlation between the structure and function can be obtained by making alignment so that homologous parts become as large as possible. However, even for proteins with the same function, the homology is not so high in general when the biological species are different. Thus, the above-mentioned methods which depend on alignment are not helpful at all for many proteins whose functions are known to be the same or not.

DISCLOSURE OF INVENTION

An object of the present invention is to provide methods of predicting functions of proteins. More specifically, the object of the present invention is to provide methods to predict easily the functions and roles in organism, for proteins whose steric structures are known or predictable. Moreover, another subject of the present invention is to provide a database which is helpful for exploring shapes and properties of ligand binding site of proteins from the side of bio-active compounds (ligands).

As a result of zealous endeavor to solve above-mentioned subjects, the inventors of the present invention found that the functions of proteins without known functions can be predicted with good accuracy by preparing a three-dimensional structure database which stores bio-active compounds capable of binding as ligands with target proteins with known biological functions, judging capability of complex formation between the proteins without known functions and each bio-active compound in the database, and selecting bio-active compounds with high capability of complex formation as ligand candidates. The present invention was achieved based on these findings.

The present invention thus provides methods of predicting biological functions of query proteins whose steric structures are known or predictable, using a three-dimensional structure database which stores one or more bio-active compounds which bind to target proteins with known biological functions, which comprises the steps of:

(1) extracting bio-active compounds capable of binding to said query protein from said database as ligand candidates, based on the capability of complex formation between the query protein and the bio-active compounds; and (2) predicting that biological functions of the query protein are identical or similar to the biological functions of the target proteins to which said ligand candidates bind.

According to a preferred embodiment of the present invention, the above-mentioned method comprises the steps of:

(3) extracting one or more ligand binding sites for the query protein;

(4) exploring the most stable complex formed with the ligand binding sites of the query protein for each bio-active compound included in the database;

(5) extracting bio-active compounds which satisfy hit conditions preset, based on the stabilities and structural features of the most stable complexes;

(6) extracting further, as required, bio-active compounds from the bio-active compounds extracted in step (5) which satisfy hit conditions different from those in the above-mentioned step (5); and (7) predicting that biological functions of the query protein are identical or similar to the biological functions of the target protein to which said ligand candidates bind, while treating the bio-active compounds extracted in above-mentioned steps (5) or (6) as ligand candidates.

In further preferable methods of the present invention, above-mentioned steps (4) through (6) are performed automatically using the program ADAM & EVE (PCT/JP95/02219: WO96/13785: U.S. Pat. No. 6,389,378). According to other embodiments of the present invention, there are provided a method of predicting biological functions of query proteins using a three-dimensional database which stores one or more bio-active compounds which bind to target proteins with known biological functions; a method of predicting biological functions of query proteins by exploring the shapes and properties of the ligand binding sites of the query protein using one or more bio-active compounds which bind to target proteins with known biological functions which are stored in a three-dimensional database; and a method of predicting functions of query proteins by extracting ligand candidates for the query protein from a three-dimensional database which stores one or more bio-active compounds which bind to target proteins with known biological functions.

According to still other embodiment of the present invention, there is provided a three-dimensional database which stores one or more bio-active compounds which bind to target proteins with known biological functions and is used for each of the above-mentioned methods. According a preferred embodiment of the present invention, there is provided a database including information about the target protein for each bio-active compound, and in a further preferred embodiment, the above-mentioned database is prepared in a form which enables to perform the above-mentioned steps (4) through (6) automatically using the program ADAM&EVE (in the specification, the database is sometimes referred to as "ADAM-style database").

From other points of view, the present invention provides a method of predicting biological functions of query proteins whose steric structures are known or predictable, using a three-dimensional database which stores one or more intrinsic bio-active compounds with known bio-activities in organisms but without the knowledge of the target protein, which comprises the steps of:

(1) extracting bio-active compounds capable of binding to said query protein from said database as ligand candidates, based on the capability of complex formation between the query protein and bio-active compounds; and (8) predicting that biological functions of the query protein concern the bio-activities of said ligand.

According to a preferred embodiment of this method, there is provided the above-mentioned method comprising steps of:

(3) extracting one or more ligand binding sites for the query protein;

(4) exploring the most stable complex formed with the ligand binding sites of the query protein for each bio-active compound included in the database;

(5) extracting bio-active compounds which satisfy hit conditions preset, based on the stabilities and structural features of the most stable complexes;

(6) further extracting, as required, bio-active compounds from the bio-active compounds extracted in step (5) which satisfy hit conditions different from those in the above-mentioned step (5); and (9) predicting that biological functions of the query protein concern the bio-activity of the ligand, while treating the bio-active compounds capable of complex formation extracted in steps (5) or (6) as ligand candidates.

As a more preferred embodiment, there is provided the above-mentioned method in which steps (4) through (6) are performed automatically using the program ADAM&EVE.

Furthermore, there are provided by the present invention, a method of predicting biological functions of query proteins whose steric structures are known or predictable using a three-dimensional database which stores one or more intrinsic bio-active compounds with known bio-activities in organisms but without the knowledge of the target protein; a method of predicting biological functions of query proteins by exploring the shapes and properties of the ligand binding site of the query protein using one or more intrinsic bio-active compounds with known bio-activities in organisms but without the knowledge of the target protein stored in a three-dimensional database; and a method of predicting biological functions of query proteins by extracting ligand candidates for the query protein from a three-dimensional database which stores one or more intrinsic bio-active compounds with known bio-activities in organisms but without the knowledge of the target protein.

In addition, the present invention provides a three-dimensional database which stores one or more intrinsic bio-active compounds with known bio-activities in organisms but without the knowledge of the target protein, and which is used for the above-mentioned methods. According to a preferred embodiment of the present invention, there is provided a database including the information about bio-activity of each bio-active compound, and according to a more preferred embodiment, the above-mentioned database is prepared in a form which enables to perform the above-mentioned steps (4) through (6) automatically using the program ADAM&EVE.

MOST PREFERRED EMBODIMENT FOR CARRYING OUT THE INVENTION

[Preparation of Database]

Figure 1:
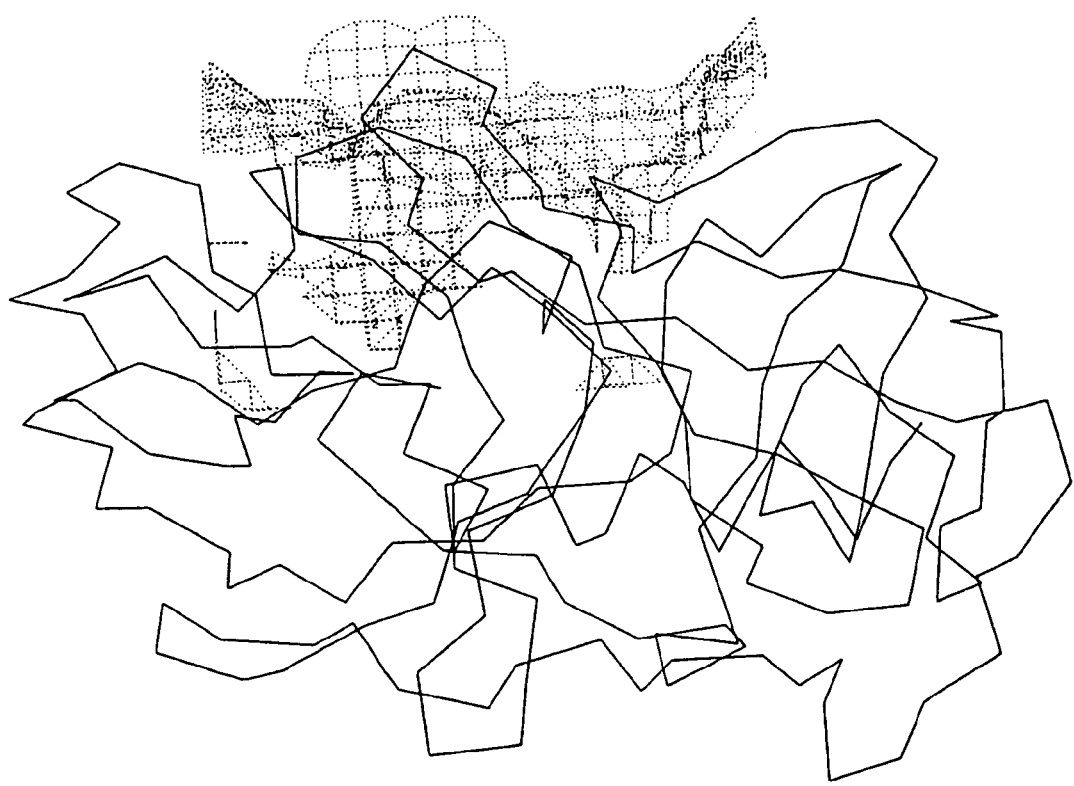
FIG. 1 shows the three-dimensional structure and ligand binding sites of bovine trypsin.

For carrying out the methods of the present invention, it is preferable to prepare in advance a three-dimensional database which stores bio-active compounds which bind as ligands to target proteins with known biological functions. The kinds of bio-active compounds are not particularly limited, for example, various bio-active substances which exist in organism, for example, transmitters (receptor substrate), enzyme substrates and enzyme products, vitamins, hormones, autacoids, co-enzymes, amino acids, bio-active peptides, nucleotides, monosaccharides in glycolytic pathway, or organic acids, as well as medicinal molecules, enzyme inhibitors, or toxins, which do not originally exist in organism, may be acceptable. Moreover, not only substances with low molecular weight but also compounds with high molecular weight such as proteins, nucleic acids like RNA or DNA, or polysaccharides may be acceptable.

In order to increase the accuracy of prediction of the methods of the present invention, it is desirable to store a lot of bio-active compounds in the above-mentioned database so that diverse biological functions are covered. It is also desirable to store as many bio-active compounds as possible with various molecular skeletons for each bio-activity, although it is sufficient to store at least one typical bio-active compound for one bio-activity in the database. Furthermore, one may prepare more than two kinds of appropriate databases, and select a desirable database and use it for the methods of the present invention.

For each bio-active compound stored in the database, it is desirable to store additional information such as information about the structure of compounds; information about the binding with target proteins; information about the biological functions of target proteins; information about the bio-activity of the compounds in case the target protein is unknown. Examples of these information include one or more kinds of information selected from the following group, comprising: name of the compound; number of constituting atoms and molecular weight; element name of each atom; two-dimensional coordinates and three-dimensional coordinates; atom types for force-field calculation; atomic charge; bonding relations; modeling method; conformation; role; bio-activity; name of target protein; subunit or domain; function classification; biological species; binding constant or sub-type specificity; and steric structure information.

In the database of the present invention, it is preferable that all of these are added as information. However, information about bio-active substances is not limited to the above-mentioned items, and one or more of the items may be substituted by other information. Furthermore, other information may be added to the above-mentioned information as required. Concerning these information, it is not always necessary to store them in a single database, and it is acceptable as long as some relationships are retained, for example, by including tag information which points to record or data in each database. In the following, each information is explained more specifically. However, it should be understood that these are explained as examples and persons skilled in the art can appropriately select them.

As "compound name", any names such as common name, trade name, development code, IUPAC nomenclature may be used so long as it can identify the bio-active compound. "Number of constituting atoms" is the number of each constituting element included in the bio-active compound, which may be expressed, for example, like $C_{24}H_{20}O_2$. For "three-dimensional coordinates", those expressed by orthogonal axes (x, y, z) in angstrom unit are preferable. "Atom types for force-field calculation" mean symbols or numbers for further classifying elements based on orbital hybridization and the like, which are used for calculating force-field energy. "Atomic charge" is the formal charge assigned on each atom to calculate electrostatic interaction energy in the force-field energy, and "bonding relation" is the information showing which atom forms a covalent bond with which number atom in the molecule, and how many the order of the bond is.

"Modeling method" is an information which indicates the origin of the three-dimensional structure of bio-active compounds, and includes information such as whether the three-dimensional structure is derived from a sole crystal structure or whether the three-dimensional structure is predicted from the two-dimensional structure using a program which convert to three dimensions. "Conformation" indicates information such as whether the conformation of the three-dimensional structure is one of the local-minimum structures obtained from the three-dimensional conversion, a sole crystal structure, or a structure determined by NMR, and whether or not the conformation is active conformation. "Role" is an information which shows that the bio-active compound acts as, for the target protein, which of enzyme substrate, enzyme reaction product, enzyme inhibitor, co-enzyme, effector, intrinsic ligand, agonist, antagonist, receptor substrate and the like. "Bio-activity" is an information about the change caused in organism upon administration of the bio-active compound.

For "target protein name", it is preferable to adopt those which generally include the functions of the protein, for example, dihydrofolate reductase, retinoid receptor and others. "Subunit or domain" is an information which indicates the subunit or domain to which bio-active compounds bind when the target protein consists of multiple subunits or domains. "Function classification" means a broad classification of function of the target protein in organism, which is exemplified by information including classification such as enzyme, trans-membrane receptor, nuclear receptor, cytokine, and transporter protein.

Information of "biological species" includes information about the biological species from which the target protein is derived. It is usually specified by taxonomy by species, genus, family, class and the like. More practically, one may use classification such that 1 for all biological species, 2 for higher animals, 3 for lower animals, 4 for prokaryotes, and 5 for plants. "Tissue" may at least include information about tissues where the target protein mainly exist and is functioning, which is exemplified by tissue names such as blood, liver and others for the case of human species. "Binding constant and sub-type specificity" may include information such as binding constant, $IC_{50}$, sub-type specificity of binding. Information about "steric structure" includes information whether three-dimensional structure of the target protein is known or not, and it is desirable to include information about whether the analytical method is crystallographic analysis or NMR analysis when three-dimensional structure is known and to include the code number in the Protein Data Bank if the structure is available therefrom.

[Extraction of Ligand Binding Site on Query Protein]

Concerning query proteins for which biological functions are to be predicted, there is no limitation about their kinds or sizes as long as their steric structures are known or predictable. For example, proteins consisting of multiple subunits or conjugated proteins like glycoprotein may be acceptable. If the three-dimensional structure analysis has been performed for the query protein by crystallographic or NMR method, data on the steric structure can be used directly. Alternatively, the steric structure may be predicted by homology modeling method and the like, using steric structures of homologous proteins as templates.

In order to judge capability of complex formation between the query protein and bio-active compounds in the database, one or more sites in the query protein molecule are extracted as candidates for the ligand binding sites. Generally, this step may be performed interactively by rotating the query protein molecule on computer graphics display and judging visually the sizes and depths of the sites like a pocket or a cavity on the molecular surface that have characteristic shapes and properties to be ligand binding sites. Alternatively, it is also possible to explore these sites automatically. If more than two candidate sites are found on the molecular surface of the query protein, the following exploration steps may be performed regarding each as a ligand binding site.

[Exploration of Stable Complex Formed Between Bio-active Compound and Query Protein]

Judgment of capability of complex formation is conducted between one or more ligand binding sites found in the query protein and each bio-active compound stored in the database. Capability of complex formation may be judged, for example, based on the stability (such as low energy value) and structural features of the complex after forming one or more complexes by binding one of the bio-active compounds stored in the database to the ligand binding site on the query protein. In order to explore multiple stable complexes effectively which are formed between the bio-active compounds and the ligand binding site of the query protein, a simulation called docking study may be utilized.

This method generally includes a process of displaying the ligand binding sites of a protein with a known structure on computer graphics display, and a process of exploring locations for stable binding by rotating and translating the molecule to be bound, with these processes usually conducted interactively. For the molecules with flexible conformation which have rotatable bonds, it is preferable to include a process of exploring stable locations while varying the conformation. After obtaining several locations which may lead to stable binding, it is possible to predict the most stable structure of the complex by performing energy calculation and optimization as required.

As a programs for the docking study, a program developed by Tomioka and others (GREEN) may be suitably employed, for example (Tomioka, N. and Itai, A., J. Comput.-Aided Mol. Design, 8, pp. 347–366, 1994). However, since a freedom concerning the rotation and translation of molecules and a freedom of conformation are coupled together, there are cases in which the above-mentioned interactive method is not sufficient for predicting the most stable structure with comprehension of all possible combinations. As a method of exploring the most stable structure of complexes while solving such problems, a program by Mizutani and others (ADAM), which performs docking automatically, can be suitably employed (Mizutani, Y. M. et al., J. Mol. Biol., 243, pp. 310–326, 1994; U.S. Pat. No. 5,642,292; PCT/JP93/0365).

When the program ADAM is employed, it is possible to explore several to several dozens of stable complex structures including the structure of the most stable complex effectively out of tremendous amount of complex structures resulting from the freedoms of binding mode and conformation, and it is possible to output automatically the complex structures obtained from the exploration, sorted in an order of their stabilities and other indices. The program ADAM, whose characteristics is high reliability and accuracy, includes a process of structure optimization with location and torsion angles varied continuously by means of repeated energy minimization, which is conducted after comprehension of approximate possibility of bonding mode and ligand conformation based on the geometrical condition of hydrogen bond formation.

In order to predict complex structures using the program ADAM, it is generally necessary to specify atom-type number and atomic charge of each atom of the bio-active compound, which is used for force-field energy calculation, classification number of hydrogen bonding functional groups for heteroatoms, initial value, final value, and increment value of torsion angle for rotatable bonds, which is used for generation of conformation, as well as the three-dimensional coordinates of the query protein and the bio-active compound. These parameters can be input interactively on computer graphics display when a bio-active compound included in the database is processed one by one using the program ADAM.

[Extraction of Bio-active Compounds to be Ligand Candidates]

By evaluating capability of complex formation between each bio-active compound and the query protein, it is possible to extract compounds that can bind to the query protein stably as ligand candidates, out of the bio-active compounds stored in the database. In the most preferable embodiment, the above-mentioned exploration process of complex structures and extraction process of ligand candidates may be conducted automatically in a consecutive process using the program ADAM&EVE (PCT/JP95/02219: WO96/13785).

When the program ADAM&EVE is employed, only a complex which is most stable (most stable complex) is explored automatically out of the complexes formed with the query protein, for each of the diverse and a lot of numbers of bio-active compounds stored in the database. After that, a judgement is given to that most stable complex whether it satisfies the criteria of selection (hit conditions) preset, and then one or more bio-active compounds satisfying the criteria are extracted as ligand candidates. As for hit conditions, parameters regarding the stabilities of the complexes (energy values) and regarding the structural features may be generally adopted. For example, value of intermolecular interaction energy, number of hydrogen bonds, molecular weight, number of atoms, number of rings, ionic bonding or hydrogen bonding with specific functional groups in the proteins may be specified arbitrarily.

When the exploration process of complex structures and extraction process of ligand candidates are conducted by the program ADAM&EVE, it is desirable to include in the database, coordinates of hydrogen atoms, atom-type number and atomic charge for each atom of bio-active compound, which is used for the force-field energy calculation, classification number of hydrogen-bonding functional groups for heteroatoms, rotatable bond and the information on their rotation (initial value, final value, increment value of torsion angle) and the like, as well as the three-dimensional coordinates of the query protein and the bio-active compound, so that diverse and many numbers of bio-active compounds stored in the database can be processed automatically. A database which includes these information and suitable for the program ADAM&EVE is particularly preferable embodiment of the present invention.

By using ordinary three-dimensional databases which include information about element name, three-dimensional coordinates and bonding relation for each constituting atom of the bio-active compounds, it is possible to prepare above-mentioned preferred database suitable for the program ADAM&EVE (ADAM-style database). Since the preparation of ADAM-style database is described in detail, for example, in PCT International Publication WO96/13785, those skilled in the art can easily prepare the database following that procedures or with proper modification and alteration as required. For example, it is possible to assign above-mentioned information automatically after reading the ordinary three-dimensional structure database. If said database does not include the information on three-dimensional coordinates of hydrogen atoms, hydrogen atoms need to be added automatically by calculating their expected position for predicting the most stable structure correctly. If the position of a hydrogen atom cannot be predicted due to a bond rotation, it is desirable to place the hydrogen atom at an extended position in trans form.

As a preferable method of preparation of the database and addition of the above-mentioned information, an example includes a method in which chemical structures are input by using the ISIS program of MDL company, which is used as a standard for managing market compounds and inhouse compounds, a database is prepared in the form of two-dimensional Molfile of MDL company, structures are transformed automatically to three-dimension by a three-dimensional conversion program, and then above-mentioned information is assigned automatically. However, the database of the present invention is not limited to such prepared with this method.

By selecting hit conditions used in the extraction process of ligand candidates appropriately, it is possible to control the number of the ligand candidates to be extracted. In order to perform the extraction of ligand candidates rapidly and accurately, it is preferable to conduct the extraction process with more than two steps of operation. For example, at the first extraction step, all bio-active compounds with possibility to be a ligand candidate are extracted by applying relatively moderate hit conditions, and at the next extraction step, the most probable one or more most stable complexes can be selected by setting more strict hit condition based on the energy of the complex, number of hydrogen bonds, and other information.

[Prediction of Function of Query Protein]

Bio-active compounds constituting the most stable complexes that satisfied the hit conditions (ligand candidates) are capable of binding stably to the query protein as ligands. That is, the query protein possesses a ligand binding site identical or analogous to the target protein to which the ligand candidates bind, and accordingly, it is highly probable that the query protein and said target protein have identical or analogous biological functions. It can be also predicted that the role of said bio-active compounds to the query protein is identical or analogous to the role to the target protein (for example, a role of enzyme substrate, receptor substrate and the like). If the target protein is identical for several extracted ligand candidates with different chemical structures, the above-mentioned prediction result is highly reliable.

For example, if retinoic acid is extracted as a ligand candidate from a database containing various bio-active compounds, it can be predicted that the query protein has a function as retinoid receptor and that retinoic acid has a role as an agonist or antagonist to the query protein. Even if identity or analogy to specific target protein cannot be predicted, there is a possibility of predicting the functions of query protein. For example, if a bio-active compound like co-enzyme NADPH which can bind to various biopolymers is extracted as a ligand candidate, it can be predicted that the query protein has either function of oxidation-reduction enzyme utilizing NADPH as co-enzyme or function of enzyme or receptor regulated by NADPH. In other case, if an intrinsic bio-active compound with known bio-activities in organisms but without the knowledge of the target protein is extracted as a ligand candidate, it is probable that the query protein is a novel receptor or enzyme to which the bio-active compound act as an intrinsic ligand.

As an example of preferred embodiment of prediction methods of the present invention, practical operating procedures using the program ADAM&EVE are shown on the following scheme. However, the methods of the present invention are not limited to the following methods.

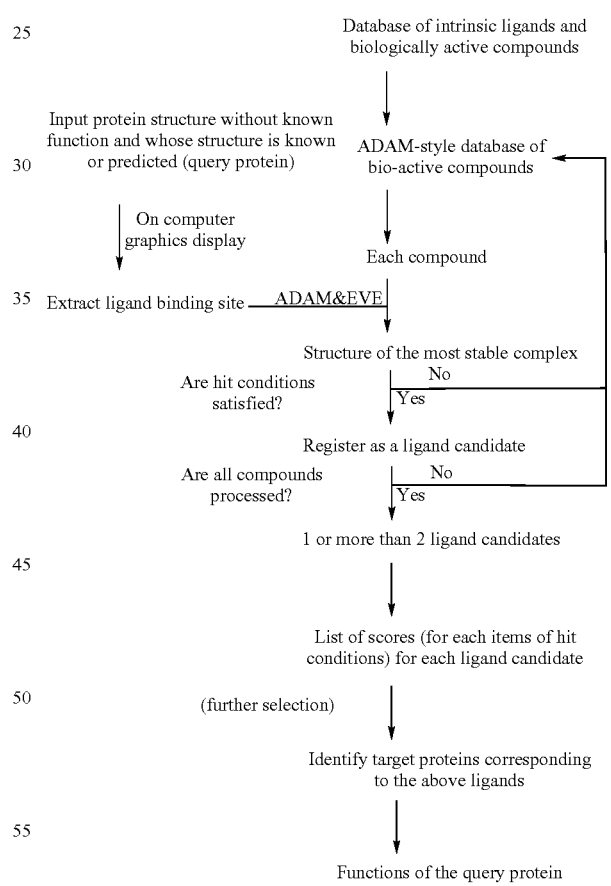

Following the above-mentioned scheme, each step is explained

1. Select intrinsic ligand compounds in organism such as enzyme substrate, enzymatic products, co-enzymes, signal transducing substances, and hormones, and bio-active compounds whose target proteins are known. Make a database of the present invention by inputting compound names, two-dimensional structures, and other information. Furthermore, input information about the target protein for each of the bio-active compounds.
2. Convert two-dimensional structures in the above-mentioned database to three-dimensional structures and create ADAM-style database by adding necessary data automatically.
3. Input three-dimensional structure of a query protein.
4. Specify one or more ligand binding sites (candidate sites) interactively on computer graphics display, and calculate information about three-dimensional grid points, hydrogen bonding, and dummy atoms which is necessary for the calculation by the program ADAM&EVE.
5. Set hit conditions.
6. Select one bio-active compound from the database.
7. Predict the structure of the most stable complex between said bio-active compound and the query protein.
8. Judge whether the structure of the most stable complex described above satisfies the hit conditions.
9. If the hit conditions are satisfied, add said bio-active compound to a ligand candidate group (first extraction group) as a hit and keep its coordinate data and others.
10. Go back to step 6, predict structures of the most stable complexes for other bio-active compounds, and repeat steps 6 through 9 until no more bio-active compound remains to be processed.
11. Concerning the bio-active compounds included in the ligand candidate group (first extraction group), output a list containing the number of compounds, energy value at each complex structure, the number of hydrogen bonds and others.
12. Reduce the number of bio-active compounds included in the ligand candidate group to a moderate number. As methods for this selection, employ either one of the following methods or combination of more than two methods selected from the followings: a method to select specified numbers of compounds based on ranking; a method to select with more strict hit condition; a method to select interactively on computer graphics display; a method to select with hit condition set by different physical or chemical properties or different computational procedures; and others.
13. Select finally a small numbers of ligand candidates. It is desirable to inspect structure of the complex for each ligand candidates on computer graphics display.
14. Output the classification and biological function of the target protein for each ligand candidate from the database.
15. Predict one or more biological functions for the query protein.

EXAMPLE

An example is provided below to describe the present invention more specifically. However, the scope of the present invention is not limited to the example below.

Example 1

We constructed a small database including bio-active compounds shown in Table 1, and explored capability of binding to a protein with known three-dimensional structure for each bio-active compound contained in the database. Although methods of the present invention can be applied in principle to query proteins without known functions, we used bovine trypsin as a query protein assuming that its function is unknown, and investigated whether or not "nafamostat", which is a trypsin inhibitor, is selected as a ligand candidate. The three-dimensional structure of bovine trypsin and its ligand binding site are shown in FIG. 1.

TABLE 1

| Bio-active compound | Target biopolymers |
|---|---|
| Methotrexate | Dihydrofolate reductase |
| Retinoic acid | Retinoid receptor |
| Nafamostat | Trypsin |
| Indomethacin | Cyclooxygenase |
| Donepezil (E2020) | Acetylcholinesterase |
| Phorbol ester | Protein kinase C |
| Morphine | Opioid receptor |
| Estradiol | Estrogen receptor |

As a result of exploration of the database, nafamostat was selected as a ligand candidate and the compound was shown to bind to the query protein stably.

Figure 2:
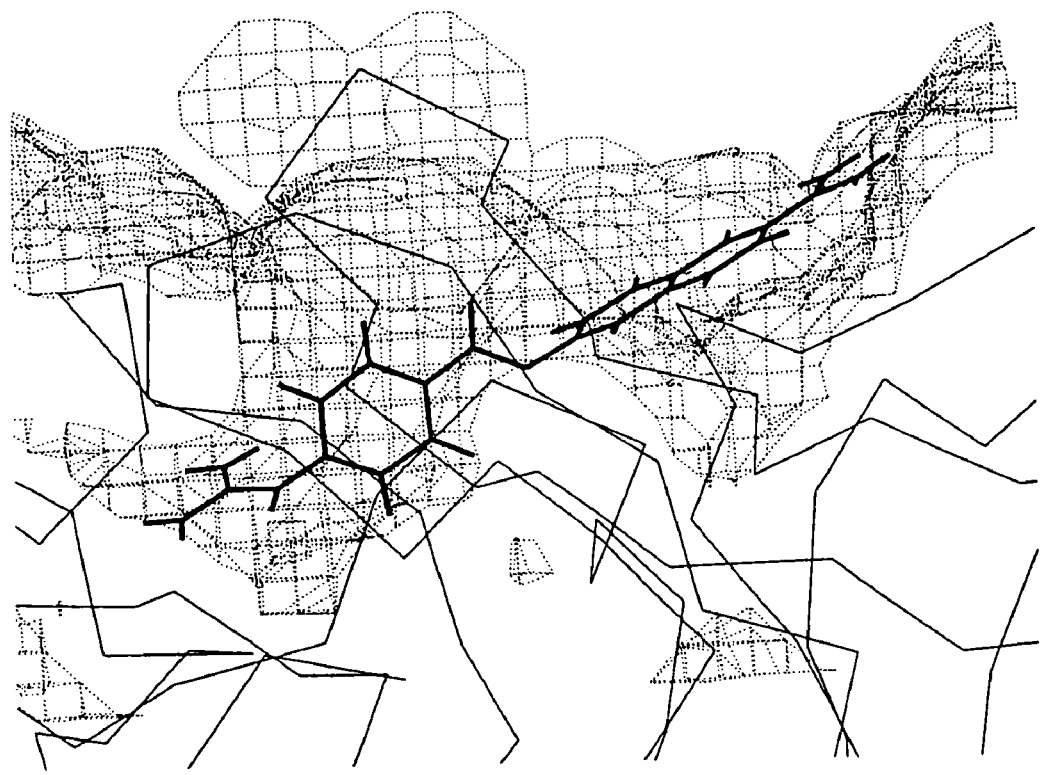
FIG. 2 shows the binding mode of nafamostat extracted from the database as a ligand candidate.

The binding mode of nafamostat to the ligand-binding site is shown in FIG. 2. Indomethacin was predicted to have possibility to form a complex, albeit a rather unstable one, and all other compounds was judged not having capability of complex formation (Table 2). From the result of this exploration, the function of the query protein was predicted to be identical or similar to trypsin, which is the target protein of nafamostat.

TABLE 2

| Bio-active compound | Intermolecular Interaction (Kcal/mol) | Number of intermolecular hydrogen bonds |
|---|---|---|
| Methotrexate | NA | NA |
| Retinoic acid | NA | NA |
| Nafamostat | −39.6 | 5 |
| Indomethacin | −29.9 | 2 |
| Donepezil (E2020) | NA | NA |
| Phorbol ester | NA | NA |
| Morphine | NA | NA |
| Estradiol | NA | NA |

INDUSTRIAL APPLICABILITY

According to the methods of the present invention, functions of protein without known functions can be predicted rapidly and accurately. The database of the present invention is useful for conducting the above methods efficiently.

What is claimed is:
1. A method of determining a biological function of one or more query proteins having predetermined or predictable steric structures using a three-dimensional structure database comprising:
  (a) selecting at least one bio-active compound capable of binding to said query protein as ligand candidates from said database based on the capability of complex formation between the query protein and bio-active compound; and
  (b) determining that a biological function of the query protein is potentially identical or similar to the biological functions of proteins with predetermined biological functions to which said ligand candidates bind wherein the database comprises the structure of at least one bio-active compound which binds to proteins with predetermined biological functions
  (c) outputting the biological function of proteins with predetermined biological function as possible functions of the query protein.

2. The method of claim 1, further comprising:
(a) identifying at least one ligand binding site for the query protein;
(b) exploring the most stable complex formed between the ligand binding site of the query protein and each bio-active compound in the database;
(c) selecting at least one bio-active compound which satisfies preset hit conditions based on the stability and structural features of the most stable complex;
(d) optionally further selecting at least one bio-active compound from the bio-active compounds selected in (c) which satisfies hit conditions different from those in (c); and
(e) determining that a biological function of the query protein are potentially identical or similar to the biological functions of proteins with predetermined biological functions to which said ligand candidates bind while treating the bio-active compounds capable of complex formation extracted in (c) or (d) as ligand candidates.

3. A method of determining a biological function of one or more query proteins having predetermined or predictable steric structures comprising using a three-dimensional structure database storing the structure of at least one bio-active compound having predetermined bio-activity in an organism which comprises:
(a) selecting at least one bio-active compound capable of binding to the query protein as ligand candidates from the database based on the capability of complex formation between the query protein and bio-active compound; and
(b) determining that the biological functions of the query protein are potentially identical or similar to the bio-activity of said ligand.

4. The method of claim 3, further comprising:
(a) identifying at least one ligand binding site for the query protein;
(b) exploring the most stable complex formed between the ligand binding site of the query protein and each bio-active compound in the database;
(c) selecting at least one bio-active compound which satisfies preset hit conditions based on the stability and structural features of the most stable complex;
(d) optionally further selecting at least one bio-active compound from the bio-active compounds selected in (c) which satisfies hit conditions different from those in (c); and
(e) determining that the biological functions of the query protein are related to the bio-activity of said ligand while treating the bio-active compounds capable of complex formation extracted selected in (c) or (d) as ligand candidates.

* * * * *

UNITED STATES PATENT AND TRADEMARK OFFICE
CERTIFICATE OF CORRECTION

PATENT NO. : 7,286,940 B2
APPLICATION NO. : 09/985652
DATED : October 23, 2007
INVENTOR(S) : Akiko Itai It is certified that error appears in the above-identified patent and that said Letters Patent is hereby corrected as shown below:

On the cover page of the printed patent, under Other Publications, col. 2 line 25, please make the following change: Nishibata, Y. Automatic In Column 13, Line 15 of the printed patent, change "are" to --is--.

In Column 14, Line 25 of the printed patent, delete "extracted".

Signed and Sealed this

Tenth Day of March, 2009

JOHN DOLL
*Acting Director of the United States Patent and Trademark Office*